US008958067B2

(12) United States Patent
Shimmura et al.

(10) Patent No.: US 8,958,067 B2
(45) Date of Patent: Feb. 17, 2015

(54) LIGHT SCATTERING PARTICLE COUNTER

(71) Applicant: Rion Co., Ltd., Tokyo (JP)

(72) Inventors: Masaki Shimmura, Tokyo (JP); Takehiro Imai, Tokyo (JP); Takuya Tabuchi, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 0 days.

(21) Appl. No.: 14/072,331

(22) Filed: Nov. 5, 2013

(65) Prior Publication Data

US 2014/0285802 A1   Sep. 25, 2014

(30) Foreign Application Priority Data

Nov. 6, 2012   (JP) ................................. 2012-244372

(51) Int. Cl.
*G01N 21/00*   (2006.01)
*G01N 15/02*   (2006.01)

(52) U.S. Cl.
CPC .................................. *G01N 15/0211* (2013.01)
USPC ......................................................... 356/343

(58) Field of Classification Search
USPC ......................................................... 356/343
See application file for complete search history.

(56) References Cited

U.S. PATENT DOCUMENTS

| | | | | |
|---|---|---|---|---|
| 3,705,771 | A  * | 12/1972 | Friedman et al. | 356/39 |
| 3,785,735 | A  * | 1/1974 | Friedman et al. | 356/39 |
| 7,127,356 | B2 * | 10/2006 | Nicoli et al. | 702/26 |
| 7,496,463 | B2 * | 2/2009 | Nicoli et al. | 702/104 |
| 7,709,821 | B2 * | 5/2010 | Casstevens et al. | 250/573 |
| 2004/0011975 | A1 * | 1/2004 | Nicoli et al. | 250/574 |
| 2005/0021244 | A1 * | 1/2005 | Nicoli et al. | 702/29 |

* cited by examiner

*Primary Examiner* — Roy M Punnoose
(74) *Attorney, Agent, or Firm* — Sheridan Ross P.C.

(57) ABSTRACT

A light scattering particle counter that improves the signal-to-noise ratio by attenuating the high frequency noise component while suppressing the attenuation of the signal component by irradiating a sample fluid with a laser beam La to form a particle detection area, detecting a particle with a multi-channel light detecting element that receives scattered light Ls from a particle passing through the particle detection area, and with low pass filters having time constants τc, τm, τe that are set to depend on beam diameter of the laser beam La and flow velocity of the fluid which flows through each divided area, to count particles in the sample fluid.

2 Claims, 4 Drawing Sheets

(a)　　　　　　　　　(b)

(c)

LIGHT SCATTERING PARTICLE COUNTER

CROSS REFERENCE TO RELATED APPLICATIONS

This application claims the benefit of Japanese Patent Application No. 2012-244372 filed Nov. 6, 2012, the entire disclosure of which is incorporated herein by reference.

FIELD OF THE INVENTION

This invention relates to a light scattering particle counter which receives scattered light from particles passing through the particle detection area using a multi-channel light detecting element, and detects the particles.

BACKGROUND ART

In a light scattering liquid-borne particle counter, it is known that the scattered light caused by the sample liquid itself contributes to the noise. Generally, fluctuation of scattered light from the sample liquid itself is superimposed on the scattered light of the object particles detected by the particle counter. The frequency of an output signal from the light detecting element that detected the scattered light from the sample liquid itself is higher than the frequency of an output signal from the light detecting element that detected the scattered light from the particles. The noise due to the scattered light from the sample liquid itself is attenuated by processing the output signal from the light detecting element with low pass filters.

DISCLOSURE OF INVENTION

Problems Solved by the Invention

As shown in FIG. 1, in an L-form flow cell 11, the flow velocity of the sample liquid is different depending on its position, the flow velocity at the center portion C of the particle detection area 13, which is located in the center of the flow path 12, is faster than the flow velocity at the side portions E of the particle detection area 13 near the wall surface W. Also, the laser light La emitted from the laser light source 14 is narrowed down by the focal depth of an irradiation light forming lens 15, the laser beam La is narrower at the center portion C than at the side portions E of the particle detection area 13. In other words, the width (beam size) of the laser light La is narrower at the center portion C than at the side portions E. Consequently, the energy density of the laser beam La is higher, and the optical intensity is increased, at the center portion C of the particle detection area 13.

Accordingly, assuming a case in which particles of the same diameter pass through the center portion C and the side portion E of the detection area 13. As shown in FIG. 2(a), when the particles pass through the center portion C of the particle detection area 13, in the waveform of an output signal Pc from the light detecting element detecting the scattered light from the particles, the pulse signal has a high peak voltage and short duration Tc. The output signal has a signal component Sc and a high-frequency noise component N. Conversely when the particles pass the side portions E of the particle detection area 13, in the waveform of an output signal Pe from the light detecting element detecting the scattered light from the particles, the pulse signal has a low peak voltage and long duration Te. The output signal has a signal component Se and a high-frequency noise component N.

The high frequency noise component N can be sufficiently attenuated by using low pass filters which has a time constant such that the high frequency noise component N can be sufficiently attenuated, as shown in FIG. 2(b). In addition, here the signal component Se of the particles passing the side portions E close to the wall surface W of the particle detection area 13 may not be attenuated. However, the signal component Sc of the particle passing through the center portion C of the particle detection area 13 may be attenuated.

On the other hand, when the time constant of the low pass filters is set not to attenuate the signal component Sc, as shown in FIG. 2(c), the signal component Sc of the particle passing through the center portion C of the particle detection area 13 is not attenuated. However, the high frequency noise component N may not be sufficiently attenuated. This is because, the signal component Se of the particles diminishes as they come closer to the side portion E of the particle detection area 13, which is near to the wall surface W. Thus, the SN ratio is reduced and the detection sensitivity also decreases.

The purpose of the present invention is to offer a light scattering particle counter which can increase the SN ratio by setting the optimum time constant value of low pass filters according to the position of the particle detection area.

Means For Solving Problems

In order to solve the above problem, a light scattering particle counter which irradiates a light beam to a sample fluid containing particles and forms a particle detection area, a multi-channel light detecting element detects scattered light from a particle passing through the particle detection area and detects the particle. It is characterized in that by using a multi-channel light detecting element, the particle detection area is divided into plural areas and the scattered light is detected by each and every divided light detecting element, the time constant of low pass filters is set at the value corresponding to each particle detection area based on the beam diameter of a laser beam and the flow velocity of a fluid flowing through each divided particle detection area, the low pass filters processes an output signal of each light detecting element comprising the multi-channel light detecting element.

The time constant ($\tau c$) of the low pass filters which processes an output signal of the light detecting element corresponding to the center of the particle detection area may be smaller than the time constant ($\tau e$) of the low pass filters which processes an output signal of the light detecting element corresponding to the side of the particle detection area ($\tau c < \tau e$).

Effects of the Invention

According to the present invention, on processing an output signal of each light detecting element of a multi-channel light detecting element with a low pass filter, because the time constant of the low pass filters can be set depending on the position of the particle detection area, the SN ratio is improved for the whole particle detection area. In this way the particle detection sensitivity improves in comparison with the conventional methodology.

BEST MODE FOR CARRYING OUT THE INVENTION

Figure 1:
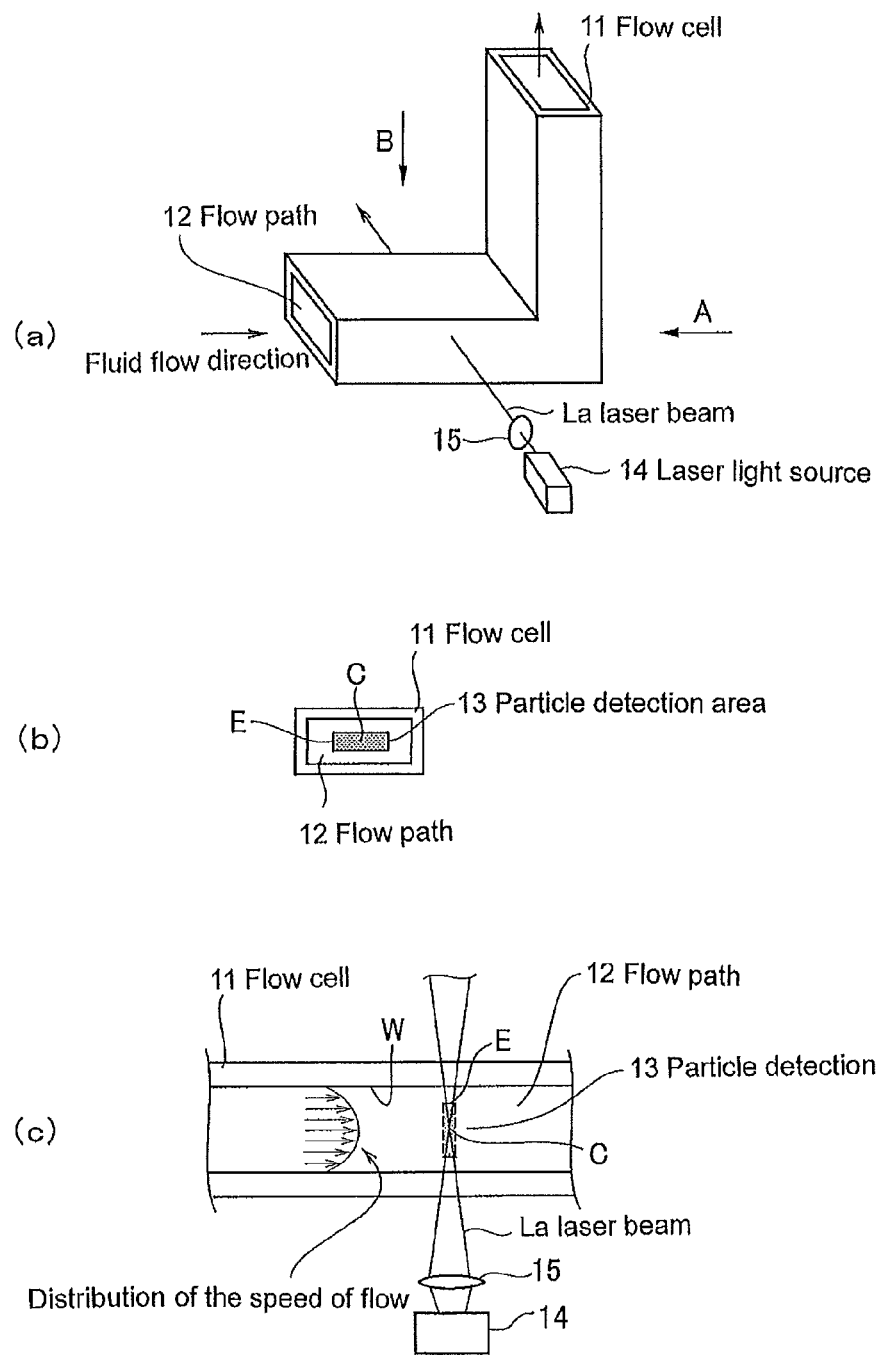
FIG. 1 An illustration of the background-art,
(a) is a perspective illustration of the L-form flow cell,
(b) is an illustration from the direction of arrow A of (a),
(c) is an illustration from the direction of arrow B of (a).
Figure 2:
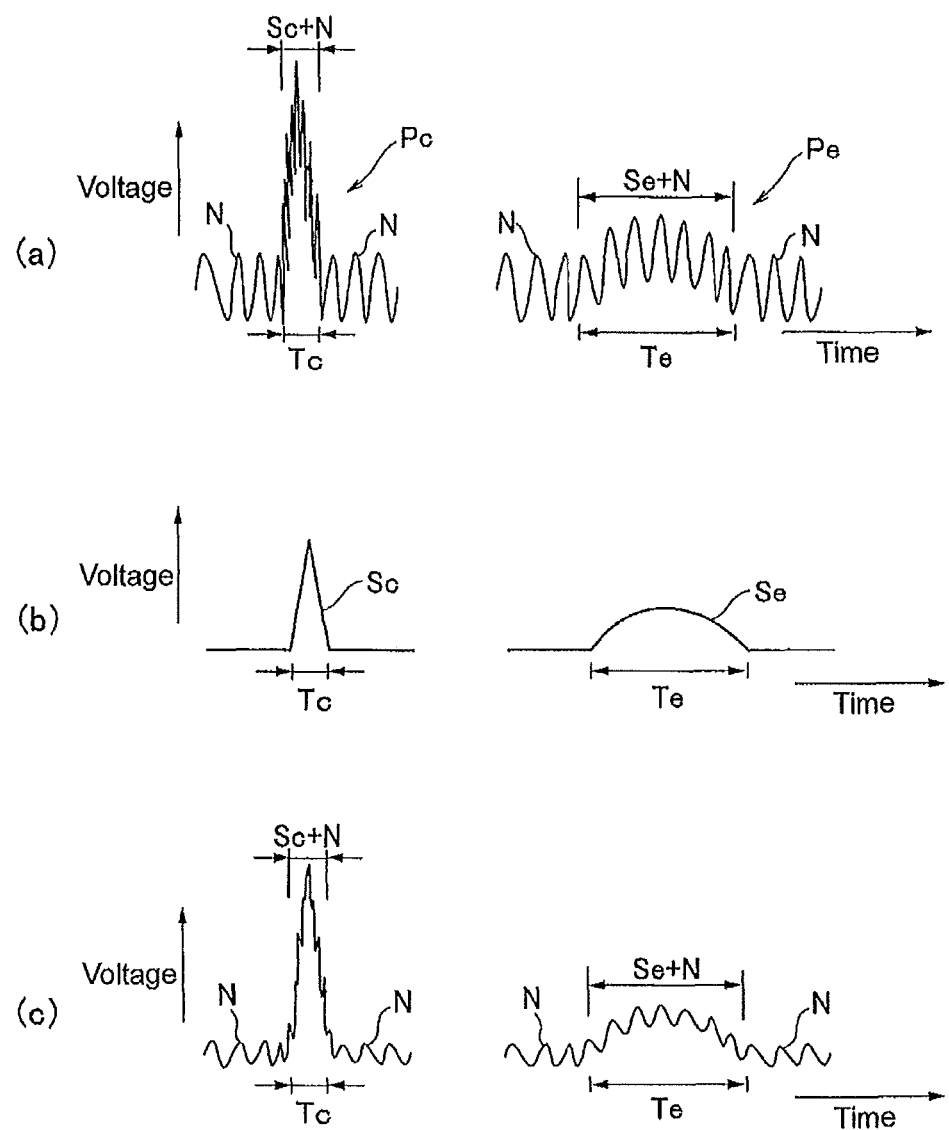
FIG. 2 An illustration of the background-art, (a) is a waveform diagram of the output signal of the light detecting element,
(b) is a waveform diagram of the signal component processed with a low pass filters which attenuates a high frequency noise component,
(c) is a waveform diagram of the signal component processed with low pass filters which substantially does not attenuate a high frequency noise component.
Figure 3:
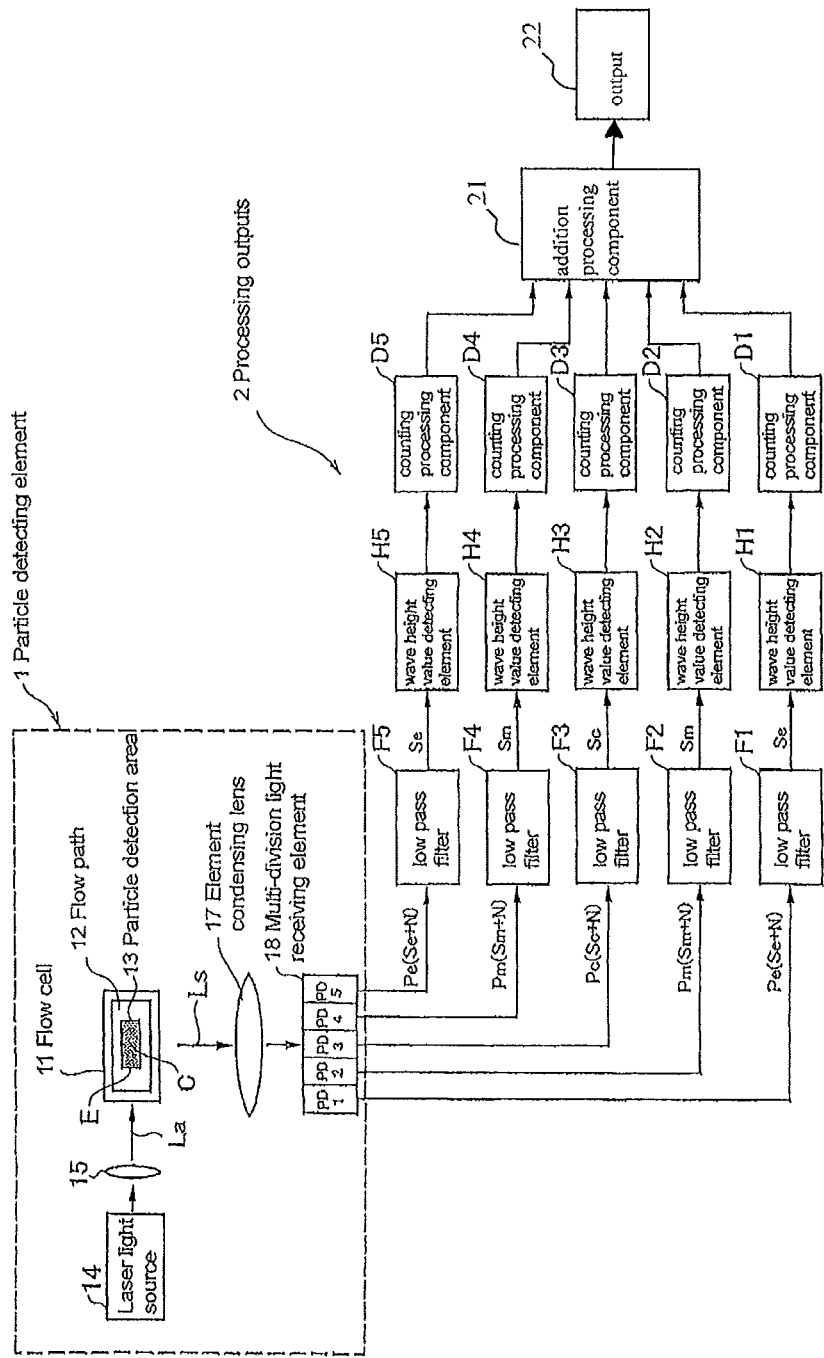
FIG. 3 A figure of the composition of the light scattering particle counter of the present invention.

As shown in FIG. 3, the light scattering particle counter of the present invention consists of a particle detecting unit 1 and a processing output unit 2. The particle detecting unit 1 detects particles in a sample liquid by using laser light La. The processing output unit 2 processes an output signal from the particle detecting unit 1 and indicates the number of particles for each particle size classification as a detection result.

The particle detecting unit 1 is provided with a flow path 12, a laser light source 14, an irradiation light forming lens 15, a condensing lens 17, and a multi-channel light detecting element 18 divided into 1 row of 5 columns. The flow path 12 is formed by an L-form flow cell 11 and drains a sample liquid. The laser light source 14 irradiates a laser beam La to the flow path 12 and forms a particle detection area 13. The condensing lens 17 condenses the scattered light Ls that is emitted from the particle which passes through the particle detection area 13. The multi-channel light detecting element 18 has light detecting elements of 1 row×5 columns, these light detecting elements convert the light which is condensed by the condensing lens 17 into voltage depending on the intensity of the light.

The multi-channel light detecting element 18 of 1 row×5 columns comprises five light detecting elements PD1, PD2, PD3, PD4, and PD5. The photoreceptor plane of each light detecting element PD1, PD2, PD3 PD4, PD5 is disposed to correspond to the respective area of the particle detection area 13.

The processing output unit 2 comprises five low pass filters F1, F2, F3, F4, F5 and five pulse height value detecting units H1, H2, H3, H4, H5. The low pass filters F1, F2, F3, F4, F5 attenuate the high frequency noise component N from the output signal of the light detecting elements PD1, PD2, PD3, PD4, PD5, and, when the output signal of the low pass filters F1, F2, F3, F4, F5 is beyond the predetermined threshold, the detecting units H1, H2, H3, H4, H5 recognize the pulse height value as being a particle.

In addition, the processing output 2 comprises five counting processing units D1, D2, D3, D4, D5, an adder unit 21 and an output unit 22. The counting processing units D1, D2, D3, D4, D5 count the particles of each particle size classification taking into consideration the pulse height value. These are detected by the pulse height value detecting units H1, H2, H3, H4, and H5. The adder unit 21 adds the calculation result processed by the counting processing units D1, D2, D3, D4, D5, and determines the number of the particles of each particle size classification. The output unit 22 indicates the number of the particles of each particle size classification in accordance with the result of the processing by the adder unit 21.

Regarding the light detecting element PD3, in the middle position of the five light detecting elements PD1, PD2, PD3, PD4, PD5, the light detecting element PD3 receives strong scattered light Ls as the particle passes through the center portion C of the particle detection area 13.

Accordingly, the pulse height value of the output signal Pc (comprised of signal component Sc and high frequency noise component N) of the light detecting element PD3 is high and the time duration Tc of the output signal Pc is short.

Therefore, a time constant $\tau c$ that does not substantially attenuate the peak of the signal component Sc but which attenuates the high frequency noise component N is set in the low pass filters F3 which processes the output signal Pc of the light detecting element PD3

Also, regarding the light detecting element PD1 and PD5, on the side positions of the five light detecting elements PD1, PD2, PD3, PD4, PD5, these light detecting elements PD1 and PD5 receive scattered light Ls as the particle passes through the side portion E of the particle detection area 13. The optical power of the scattered light Ls is relatively weaker and the flow velocity is slower than in the center portion C since the side portion E is near the wall surface W.

Accordingly, the pulse height value of the output signal Pe (comprised of signal component Se and high frequency noise component N) of the light detecting elements PD1 and PD5 is low and the time duration Te of the output signal Pe is long.

Therefore, a time constant $\tau e$ that does not substantially attenuate the peak of the signal component Se but which attenuates the high frequency noise component N is set in the low pass filters F1 and F5 which process the output signal Pe of the light detecting elements PD1 and PD5.

In addition, a time constant $\tau m$ is set for the low pass filters F2, F4 which process the output signal Pm (comprised of signal component Sm and high frequency noise component N) of PD2 and PD4.

The time constant $\tau m$ attenuates the high frequency noise component N without substantially attenuating the peak of the signal component Sm. Herein, the relationship in terms of magnitude among time constant $\tau c$, time constant $\tau m$ and time constant $\tau e$ is $\tau c < \tau m < \tau e$.

As described above, by using the multi-channel light detecting element, it becomes possible to receive the scattered light from a particle in the condition that the particle detection area 13 is divided into plural detection areas.

Also, it becomes possible to set the time constants $\tau c$, $\tau m$, $\tau e$ of the low pass filters F1, F2, F3, F4, F5 depending on the beam diameter of the laser beam La and the flow velocity of the fluid which flows through each divided area.

By setting the time constants $\tau c$, $\tau m$, and $\tau e$ of the low pass filters F1, F2, F3, F4, F5 at a value depending on each divided area, attenuation of the signal components Sc, Sm, and Se can be minimized. The high frequency noise component N due to the scattered light from the sample fluid itself can be sufficiently attenuated. As a result, the SN ratio can be increased over the whole particle detection area 13 and the detection sensitivity can be improved.

In this embodiment, the multi-channel light detecting element 18 having light detecting element of 1 row×5 columns is explained, but, it is not limited to 1 row×5 columns.

Figure 4:
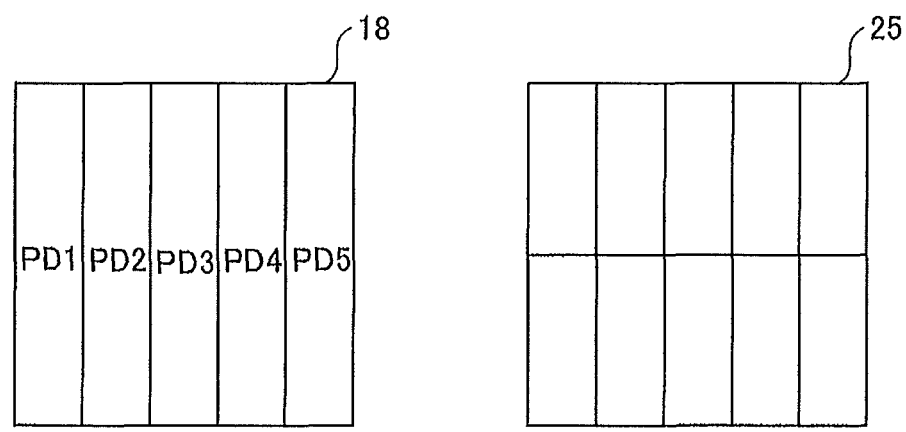
FIG. 4 A plane view showing an example of a multi-channel light detecting element,
(a) is an illustration of the multi-channel light detecting element of 1 row×5 columns
(b) is an illustration of the multi-channel light detecting element of 2 rows×5 columns
(c) is an illustration of the multi-channel light detecting element of 5 rows×5 columns
Figure 4:
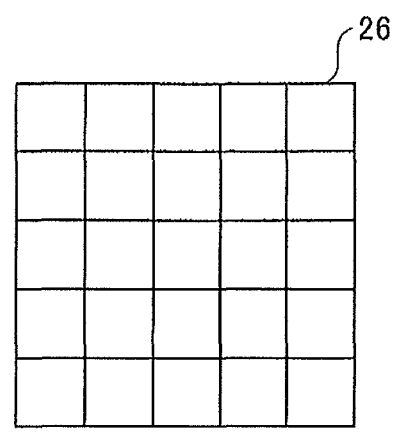

As shown in FIG. 4, other than the multi-channel light detecting element 18 (FIG. 4(a) above) of 1 row×5 columns, the multi-channel light detecting element 25 (FIG. 4(b)

above) of 2 rows×5 columns, or multi-channel light detecting element 26 (FIG. 4(*c*) above) of 5 rows×5 columns can be applied.

In the case of applying the multi-channel light detecting element 25, or 26 of 2 rows×5 columns or 5 rows×5 columns, low pass filters are provided in each of the light detecting elements which comprise the multi-channel light detecting elements 25 and 26. The time constant is set such that the respective position of the particle detection area responded to the low pass filters.

In this embodiment, the sample fluid is a liquid, but the use of a gas is equally applicable.

INDUSTRIAL APPLICABILITY

According to the present invention, it is possible to set the time constant of the low pass filters processes the output signal of each light detecting element comprising the multi-channel light detecting element responding to each particle detection area. Thus the high frequency noise component due to light produced from the sample fluid itself or the like can be sufficiently attenuated, while attenuation of the signal component is suppressed. Accordingly, the SN ratio can be increased over the whole particle detection area. As a result, a light scattering particle counter with particle detection sensitivity higher than the particle detection sensitivity of conventional counters can be offered.

Explanations of the Letters and Numerals

1 . . . particle detecting unit, 2 . . . processing output unit, 11 . . . L-form flow cells, 12 . . . flow path, 13 . . . particle detection area, 14 . . . laser light source, 15 . . . irradiation light forming lens, 17 . . . condensing lens, 18, 25, 26 . . . multi-channel light detecting element, 21 . . . addition processing components, 22 . . . output unit, C . . . center portion, D1, D2, D3, D4, D5 . . . counting processing component, E . . . side portion, F1, F2, F3, F4, F5 . . . low pass filter, H1, H2, H3, H4, H5 . . . pulse height value detecting unit, La . . . laser beam, Ls . . . scattered light, N . . . high frequency noise component, PD1, PD2, PD3, PD4, PD5 . . . light detecting element, Pc, Pm, Pe . . . output signal, Sc, Sm, Se . . . signal component, $\tau c, \tau m, \tau e$ . . . time constant

The invention claimed is:

1. A light scattering particle counter comprising:
   a light beam that irradiates a sample fluid to form a particle detection area;
   a multi-channel light detecting element that receives scattered light from a particle passing through the particle detection area and detects the particle; and,
   low pass filters having a time constant that are set to a value that corresponds to each particle detection area based on the beam diameter and flow velocity of fluid flowing through each divided particle detection area;
   wherein,
   the multi-channel light detecting element is configured to divide the particle detection area into a plurality of light detecting elements which are configured to detect scattered light from the particle in the sample fluid passing through the particle detection area; and,
   said low pass filters are configured to process output signal of each light detecting element of the multi-channel light detecting element to count particles in said sample fluid.

2. A light scattering particle counter according to claim 1, in which, the time constant ($\tau c$) of the low pass filters which process an output signal of the light detecting element corresponding to the center of the particle detection area is smaller than the time constant ($\tau e$) of the low pass filters which processes an output signal of the light detecting element corresponding to the side portion of the particle detection area ($\tau c < \tau e$).

* * * * *